(12) United States Patent
Baharuddin et al.

(10) Patent No.: US 10,501,407 B2
(45) Date of Patent: Dec. 10, 2019

(54) UREA MANUFACTURING METHOD AND UREA MANUFACTURING APPARATUS

(71) Applicant: Toyo Engineering Corporation, Tokyo (JP)

(72) Inventors: Maghfuri Baharuddin, Chiba (JP); Genshi Nishikawa, Chiba (JP); Haruyuki Morikawa, Chiba (JP)

(73) Assignee: Toyo Engineering Corporation, Tokyo (JP)

( * ) Notice: Subject to any disclaimer, the term of this patent is extended or adjusted under 35 U.S.C. 154(b) by 8 days.

(21) Appl. No.: 15/758,285

(22) PCT Filed: Aug. 31, 2016

(86) PCT No.: PCT/JP2016/075504
§ 371 (c)(1),
(2) Date: Mar. 7, 2018

(87) PCT Pub. No.: WO2017/043390
PCT Pub. Date: Mar. 16, 2017

(65) Prior Publication Data
US 2018/0258033 A1      Sep. 13, 2018

(30) Foreign Application Priority Data
Sep. 8, 2015   (JP) .................. 2015-176432

(51) Int. Cl.
*C07C 273/04*    (2006.01)
*B01J 19/24*     (2006.01)

(52) U.S. Cl.
CPC ........ *C07C 273/04* (2013.01); *B01J 19/2415* (2013.01); *B01J 2219/00081* (2013.01); *B01J 2219/24* (2013.01)

(58) Field of Classification Search
CPC ................................... C07C 273/04
See application file for complete search history.

(56) References Cited

U.S. PATENT DOCUMENTS 5,849,952 A      12/1998   Carloni et al.
6,518,457 B1 *   2/2003    Sakata .............. C07C 273/04
                                              564/67

(Continued)

FOREIGN PATENT DOCUMENTS

EP    0212744 A1     8/1986
GB    2196965 A  *  5/1988  ........ C07C 273/04

(Continued)

OTHER PUBLICATIONS

WIPO, Japanese International Search Authority, International Search Report in English, International Search Report and Written Opinion in Japanese, dated Oct. 11, 2016 in International Patent Application No. PCT/JP2016/075504, 8 pages.

*Primary Examiner* — Jennifer A Leung
(74) *Attorney, Agent, or Firm* — Masuvalley & Partners

(57) ABSTRACT

Method and apparatus that enable the more efficient manufacture of urea are provided. Before unreacted substances are removed from a urea synthesis solution obtained from a stripper, the urea synthesis solution is placed under pressure reduced from the synthesis pressure. Thus, a gas-liquid mixture is obtained. The gas-liquid mixture is heated with a decomposed gas from the stripper using a shell-and-tube heat exchanger, and then introduced into a purification system. In the heating, the gas-liquid mixture is introduced into the shell of the heat exchanger while the decomposed gas is introduced into the tube side of the heat exchanger.

11 Claims, 1 Drawing Sheet

(56) References Cited

U.S. PATENT DOCUMENTS

2009/0062566 A1\* 3/2009 Kojima .................. B01D 3/343
　　　　　　　　　　　　　　　　　　　　　　564/67
2015/0119603 A1 　4/2015 Van Den Tillaart et al.

FOREIGN PATENT DOCUMENTS

| JP | S61-109760 A | 5/1986 |
| JP | 63-112552 A | 5/1998 |
| JP | 2002-145850 A | 5/2002 |
| JP | 2003-104949 A | 4/2003 |

\* cited by examiner

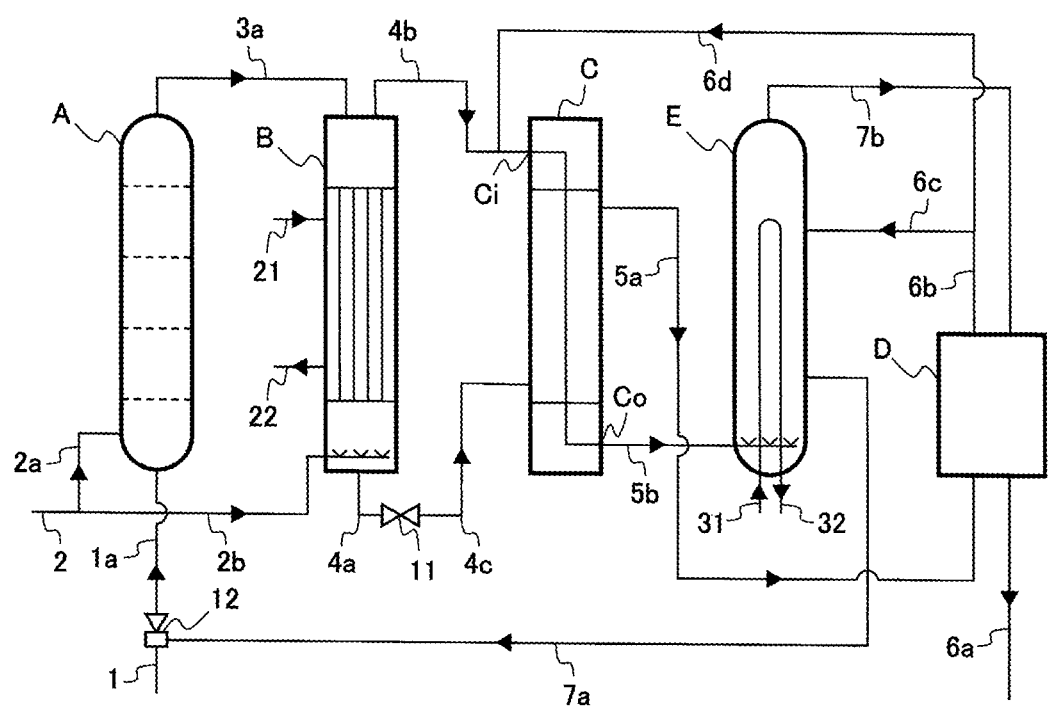

UREA MANUFACTURING METHOD AND UREA MANUFACTURING APPARATUS

RELATED APPLICATIONS

This application is the U.S. National Phase of and claims priority to International Patent Application No. PCT/JP2016/075504, International Filing Date Aug. 31, 2016, entitled Urea Production Method And Urea Production Device; which claims benefit of Japanese Application No. 2015-176432 filed Sep. 8, 2015; both of which are incorporated herein by reference in their entireties.

TECHNICAL FIELD

The present invention relates to urea manufacturing method and manufacturing apparatus, more specifically to a method and an apparatus which enable the more efficient manufacture of urea.

BACKGROUND ART

Urea is manufactured by the following method: first, ammonia ($NH_3$) and carbon dioxide ($CO_2$) are subjected to a reaction to produce ammonium carbamate ($NH_2COONH_4$) as represented by Formula (1), and then, ammonium carbamate is subjected to a dehydration reaction to produce urea ($NH_2CONH_2$) and water ($H_2O$) as represented by Formula (2).

$$2NH_3 + CO_2 \rightarrow NH_2COONH_4 \quad (1)$$

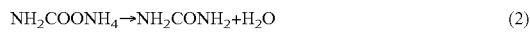

$$NH_2COONH_4 \rightarrow NH_2CONH_2 + H_2O \quad (2)$$

Both reactions are the equilibrium reaction but the reaction of Formula (1) is the exothermic reaction while the reaction of Formula (2) is the endothermic reaction. For this reason, it has been difficult to efficiently manufacture urea from the raw materials of ammonia and carbon dioxide and various devises therefore have been studied.

Patent Literature 1 has described the technique made for the purpose of reducing the amount of water to be returned to the synthesis zone. In this technique, the solution from the stripper is processed in at two stages which is conducted at medium pressure and low pressure. In this manner, the remaining unreacted substances are removed. The solution from the stripper is expanded at the expansion valve 17 and placed under reduced pressure of from 12 to 30 bar and said solution become a fluid in gas-liquid phase. The fluid is introduced into the gas-liquid separator 6, where the fluid is separated into the gas and the liquid. Of the separated gas and liquid, just the liquid is introduced into the tube side of the first high pressure condensation zone 3, which is the horizontal condensation reactor under the further reduced pressure. The liquid is discharged after being heated by the heat of condensation of the decomposed gas or the like from the stripper in the first high pressure condensation zone 3. The liquid heated by the heat of condensation is also introduced into another gas-liquid separator 7 so that gas is separated therefrom. The liquid is introduced into the contact zone 8 (corresponding to the medium-pressure decomposition column). The unreacted substances of the liquid are stripped adiabatically using the gas from the gas-liquid separator 6. The pressure is further reduced and the gas and liquid are separated from the liquid introduced into the gas-liquid separator 9. The separated liquid is introduced into the heat exchanger 10 (corresponding to low-pressure decomposition column). The gas from the gas-liquid separators is recovered, condensed, and returned to the synthesis zone (the first high pressure condensation zone 3).

Patent Literature 2 has described the method of introducing the urea synthesis solution from the stripper into the tube side of the bubble column type vertical condensation reactor, thereby heating the solution. This method enables the higher heat transfer performance than the conventional technique, and with this method, the heating can be carried out at higher temperature level (from 170 to 180° C.). For this reason, this method is featured in that the heat transfer area can be drastically reduced. However, this patent literature does not particularly mention the removal of the unreacted substances in the medium-pressure decomposing process.

CITATION LIST

Patent Literature

PATENT LITERATURE 1: EP 0212744 A Specification
PATENT LITERATURE 2: JP-A-2003-104949
PATENT LITERATURE 3: JP-A-2002-145850
PATENT LITERATURE 4: JP-A-61-109760

SUMMARY OF THE INVENTION

Problems to be Solved by the Invention

In the technique according to Patent Literature 1 Specification, the gas is separated in the gas-liquid separator 6 and then the liquid is introduced into the first high pressure condensation zone 3. In the example disclosed therein, the fluid from the gas-liquid separator 6 flows into the tube side of the first high pressure condensation zone 3. In the shell side, the decomposed gas from the stripper is condensed and the condensate is retained to produce a portion of urea. However, if the fluid to be supplied to the tube side of the first high pressure condensation zone 3 contains a large amount of gas generated by the pressure reduction, the gas and liquid are separated vertically in the channel portion, in which case the uniform distribution to each tube is difficult. Inside the tube, moreover, the gas and liquid are separated vertically, so that the heat transfer performance is deteriorated. For this reason, the gas generated by the pressure reduction needs to be separated when the gas is separated in the gas-liquid separator 6.

The gas from the gas-liquid separator 6 is introduced into the contact zone and the liquid from the gas-liquid separator 7 is stripped adiabatically. The gas from the gas-liquid separator 6 contains ammonia, carbon dioxide, and water and the concentration of ammonia and carbon dioxide is high. From the aqueous urea solution from the gas-liquid separator 7, the unreacted substances have been decomposed and removed. Accordingly, the concentration of the remaining ammonia and carbon dioxide is low. If this aqueous urea solution is brought into contact with the gas containing much ammonia and carbon dioxide adiabatically, it is considered that ammonia and carbon dioxide are easily dissolved in the aqueous urea solution. That is to say, the effect of removing the unreacted ammonia and carbon dioxide contained in the liquid by stripping the liquid cannot be expected and rather, the unreacted substances contained in the liquid increase. This leads to the larger burden in separating and recovering the unreacted substances in the downstream side, and more water is required to recover the unreacted substances.

The decomposed gas 25 and the entire amount of carbamate solution (recovered solution) via line 47 are condensed in the first condenser and thus separated into gas and liquid. The resulting liquid is then heated. In addition, a gas-liquid mixture in the shell of the first high pressure condensation zone is condensed in the tube side of the second high pressure condensation zone 4, and this produces the steam. With this structure, a large amount of off gas is generated in the shell side in the first high pressure condensation zone. In addition, the gas and liquid of the fluid are easily separated vertically in the shell. For this reason, it is necessary to provide the piping 29 and 30 to remove the gas phase and the liquid phase. In the channel portion of the second high pressure condensation zone, the gas and the liquid are introduced through different pipes; therefore, in order to mix the gas and the liquid uniformly, the channel portion needs to have enough volume.

In the method according to the Patent Literature 2, the two fluids, the generated steam and the heated urea synthesis solution, flow in the tube side of the condenser (vertical condensation reactor). This makes the structure of the channel portion complicated. In the shell side, the gas from the stripper is condensed. By having the condensate remain in the shell to cause the reaction of a portion of urea, the urea synthesis solution is obtained. However, the gas that has failed to be condensed from the condenser is separated and supplied to the downstream side, and recovered in the recovery system. The amount of this gas is preferably smaller in order to reduce the burdens in separating and recovering the unreacted substances. Increasing the temperature in the shell of the condenser to achieve this has been limited to from 170 to 180° C. according to the patent literature. Increasing the temperature over the above range is not preferable because more gas flows to the downstream side as described above. Thus, the temperature level as the heating source has been limited.

It has also been disclosed that the heat transfer area is drastically reduced by using the heat of condensation of the mixed gas from the stripper directly as the heat source in the step of separating the unreacted ammonia and carbon dioxide. However, it is difficult to generate the steam and directly heat the aqueous urea solution at the same time in the bubble column type vertical condensation reactor. Even if the difficulty is overcome, it is still difficult to reduce the heat transfer area because the temperature in the shell is limited.

As thus described, the urea manufacturing efficiency in the existing method is not necessarily sufficient and it has been desired to develop the method of manufacturing urea more efficiently.

In view of this, an object of the present invention is to provide a method and an apparatus for manufacturing urea more efficiently.

Solution to the Problems

The present inventors have examined the problem of the conventional technique. As a result of the examinations, a method has been found out in which the gas-liquid mixture is obtained from the urea synthesis solution from the stripper by placing the urea synthesis solution under pressure reduced from the synthesis pressure before removing the unreacted substances from the urea synthesis solution. Another method has been found out in which by directly heating the resulting gas-liquid mixture with the use of the decomposed gas from the stripper, the temperature of the fluid in a mixed phase is increased as much as possible. It has been made clear that the method and apparatus with such a structure have the following features. The gas-liquid mixture generated by condensing a portion of gas from the stripper is introduced into the condenser. This reduces the amount of heat to be removed in the condenser. As a result, the amount of water to be introduced into the recovery system as the solvent for absorbing medium is reduced. Thus, the urea reaction efficiency in the synthesis zone is improved. This can increase the efficiency of the urea manufacturing equipment and reduce the size of the condenser.

A urea manufacturing method of the present invention includes: a synthesis step of reacting carbon dioxide and ammonia in a reactor under a condition of excessive ammonia, thereby providing a synthesis mixture containing urea, ammonium carbamate, water, unreacted ammonia, and unreacted carbon dioxide; a decomposition step of decomposing the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea; a pressure reduction step of placing the urea synthesis solution under reduced pressure, thereby providing a gas-liquid mixture; a heating step of heating the gas-liquid mixture with the decomposed gas; a purification step of separating unreacted substances including ammonia, carbon dioxide, and water from the heated gas-liquid mixture, thereby providing a purified urea and water and recovering the separated unreacted substances; a condensation step of condensing the decomposed gas after heating the gas-liquid mixture in a condenser together with at least a portion of the unreacted substances recovered in the purification step, thereby providing a condensate; and a condensate introduction step of introducing the condensate to the reactor, wherein in the heating step, the decomposed gas is introduced into a tube side of a shell-and-tube heat exchanger while the gas-liquid mixture is introduced into a shell side of the shell-and-tube heat exchanger.

A urea manufacturing apparatus of the present invention includes: a reactor in which carbon dioxide and ammonia are reacted under a condition of excessive ammonia, thereby providing a synthesis mixture containing urea, ammonium carbamate, water, unreacted ammonia, and unreacted carbon dioxide; a stripper that decomposes the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea; a control valve for providing a gas-liquid mixture by placing the urea synthesis solution under reduced pressure; a shell-and-tube heat exchanger that heats the gas-liquid mixture with the decomposed gas; a purification system that purifies urea by separating unreacted substances including ammonia, carbon dioxide, and water from the heated gas-liquid mixture, and recovering the separated unreacted substances; a condenser that condenses the decomposed gas after heating the gas-liquid mixture, and at least a portion of the unreacted substances recovered in the purification system, thereby providing a condensate; and a condensate introduction line that introduces the condensate to the reactor, wherein the decomposed gas is introduced into a tube side of the shell-and-tube heat exchanger and the gas-liquid mixture is introduced into a shell side of the shell-and-tube heat exchanger.

Effects of the Invention

According to the present invention, the method and the apparatus that enable the more efficient manufacture of urea can be provided.

BRIEF DESCRIPTION OF THE DRAWINGS

FIG. 1 is a diagram illustrating a configuration example of a urea manufacturing apparatus according to the present invention.

DESCRIPTION OF THE EMBODIMENTS

FIG. 1 illustrates a configuration example of a urea manufacturing apparatus according to the present invention. The apparatus illustrated in FIG. 1 includes a reactor A, a stripper B, a shell-and-tube heat exchanger C, a purification system D, and a condenser E.

In the reactor A, ammonia ($NH_3$) and carbon dioxide ($CO_2$) are subjected to react to produce ammonium carbamate, and further ammonium carbamate is subjected to dehydration reaction to produce urea and water (urea synthesis step). In the urea synthesis step, ammonia is excessive in consideration of the equilibrium pressure of the synthesis mixture to be obtained. In the urea synthesis step, the molar ratio of the $NH_3$ component to the $CO_2$ component (N/C) is preferably between 3.0 and 4.0, more preferably between 3.5 and 4.0.

The $NH_3$ component contains, in addition to the actually present ammonia, ammonia converted into ammonium carbamate and ammonia converted into urea. Therefore, the molar amount of the $NH_3$ component corresponds to the total value of twice as much as the molar amount of urea, twice as much as the molar amount of ammonium carbamate, and the molar amount of ammonia. The $CO_2$ component contains, in addition to the actually present carbon dioxide, carbon dioxide converted into ammonium carbamate and carbon dioxide converted into urea. Therefore, the molar amount of the $CO_2$ component corresponds to the total value of the molar amount of urea, the molar amount of ammonium carbamate, and the molar amount of carbon dioxide.

The two stage reactions of the urea synthesis step are both the equilibrium reaction. Therefore, in the urea synthesis step, the synthesis mixture containing urea (including a small amount of biuret), ammonium carbamate, water, unreacted ammonia, and unreacted carbon dioxide is obtained. The ammonium carbamate contained in the synthesis mixture is decomposed in the next decomposition step, and the unreacted raw materials need to be separated. Therefore, it is more preferable that the conversion rate to urea in the reactor A be higher. The reactor A is accordingly operated at the high temperature (from 175 to 200° C.) and high pressure (from 130 to 200 bar).

Ammonia as the raw material is introduced into the reactor A through an ammonia introduction line 1. Carbon dioxide as the raw material is introduced into the reactor A through carbon dioxide introduction lines 2 and 2a. Carbon dioxide and ammonia are also supplied from the condenser E to be described below through a condensate introduction line 7a and a raw material introduction line 1a. The condensate introduction line 7a is connected to an ejector 12. In the ejector 12, at least a portion of the ammonia introduced as the raw material through the ammonia introduction line 1 is used as a driving fluid. The provision of the ejector 12 is not essential but since the pressure of the reactor A is higher than the pressure of the condenser E, the ejector 12, which uses at least a portion of the ammonia introduced as the raw material in the reactor as the driving fluid, is preferably provided. The same effect can be obtained even when the position of the condenser E is set high enough to compensate the pressure difference between the condenser E and the reactor A but using the ejector 12 makes the operation more stable.

The synthesis mixture obtained in the reactor A is introduced into the stripper B through a synthesis mixture line 3a. In the stripper B, the synthesis mixture is heated so that ammonium carbamate is decomposed into ammonia and carbon dioxide. And by further stripping using at least a portion of raw material carbon dioxide as an auxiliary agent, the decomposed gas containing ammonia and carbon dioxide is separated (decomposition step). However, the ammonia and carbon dioxide cannot be fully separated from urea and water in the synthesis mixture in the stripper B; therefore, the urea synthesis solution containing ammonia, carbon dioxide, water and urea is obtained. Carbon dioxide is contained in the urea synthesis solution as the ammonium carbamate generated from the reaction with ammonia, and the urea synthesis solution from the stripper B usually contains ammonia, including the ammonia as ammonium carbamate, by approximately from 10 to 15 wt %.

Carbon dioxide as the auxiliary agent in the stripping is introduced into the stripper B through carbon dioxide introduction lines 2 and 2b. The stripper B is heated by a heating medium introduced through a stripper heating medium introduction line 21. The heating medium is discharged through a stripper heating medium discharge line 22. The heating medium is usually steam (water vapor). The pressure of the steam is set to, for example, 20 bar.

The urea synthesis solution obtained in the stripper B is discharged through a urea synthesis solution line 4a connected to the bottom of the stripper B. The pressure is reduced using a control valve 11 and the discharged urea synthesis solution becomes a gas-liquid mixture (pressure reduction step). With the control valve 11, usually the pressure is reduced to between 15 and 20 bar, and thus the gas-liquid mixture with a temperature of between 130 and 140° C. is obtained. The concentration of each of ammonia and carbon dioxide contained in the gas-liquid mixture is preferably between 10 and 15 wt %.

The obtained gas-liquid mixture is introduced into a shell-and-tube heat exchanger C through a gas-liquid mixed phase fluid line 4c. The decomposed gas separated in the stripper B is introduced into the shell-and-tube heat exchanger C through a decomposed gas line 4b. Thus, the gas-liquid mixture is heated by the decomposed gas (heating step). This enables the ammonium carbamate remaining in the gas-liquid mixture to be decomposed into ammonia and carbon dioxide. Usually, in this step, the gas-liquid mixture is heated up to from 150 to 165° C.

In the present invention, in this heating step, the gas-liquid mixture is introduced into the shell side of the shell-and-tube heat exchanger C while the decomposed gas is introduced into the tube side of the shell-and-tube heat exchanger C. For supplying the decomposed gas with the high pressure into the shell side of the shell-and-tube heat exchanger C, the design pressure of the entire shell-and-tube heat exchanger C needs to be set high. Thus, the decomposed gas with the high pressure is supplied into the tube side here. The decomposed gas is introduced from a tube inlet Ci to be used to heat the gas-liquid mixture and then discharged from a tube outlet Co. From the viewpoint of heating efficiency, the decomposed gas is preferably introduced through an upper nozzle among the nozzles of the tube side of the shell-and-tube heat exchanger C.

The shell-and-tube heat exchanger C may be of either a vertical type or a horizontal type, preferably of a vertical type because the vertical type is compact and can be installed in a smaller area. In the case of using a vertical shell-and-tube heat exchanger, it is preferable to use a straight tube to enable the flow of the decomposed gas from top to bottom. This causes the condensate to flow down along the inner wall surface of the tubes and the gas to flow in the same direction. This is advantageous in that the fluid flowing in the tubes is separated into the gas and liquid less easily. Note that in the case of using a vertical shell-and-tube heat exchanger, it is preferable that the gas-liquid mixture be introduced through the lower nozzle among the nozzles of the shell (flows from below to above). In the case of using the horizontal shell-and-tube heat exchanger, using the U-shaped tube can reduce the channel portion (flange) so that the cost is low. The horizontal heat exchanger is preferably used especially when the separation of the gas and liquid in the tube is not remarkable. In this case, the upper nozzle among the nozzles of the tube side may be the gas inlet nozzle and the lower nozzle may be the outlet nozzle that discharges the gas and the condensate. The heat exchanger with such a structure discharges the solution condensed in the tubes under gravity. In the case of introducing the gas-liquid mixture into the shell, the gas-liquid mixture is introduced from the inlet nozzle at the bottom of the shell close to the tube side outlet nozzle. The gas generated by heating and the gas contained in the gas-liquid mixture at the introduction into the shell are discharged from the nozzle in the upper part of the shell and the liquid is discharged from the shell bottom opposite to the inlet nozzle.

The gas-liquid mixture heated in the shell-and-tube heat exchanger C is introduced into the purification system D through a gas-liquid mixed phase fluid line 5a. In the purification system D, the unreacted substances containing ammonia, carbon dioxide, and water is separated from the gas-liquid mixture, so that urea is purified and moreover the separated unreacted substances are recovered (purification step).

In the purification system D, the gas-liquid mixture is placed under the pressure reduced to the pressure of such a degree that is suitable to separate the unreacted substances containing ammonia, carbon dioxide, and water. Further, the fluid is heated with steam; thus, the substantial aqueous urea solution is obtained. In general, when the total amount of ammonia and carbon dioxide remaining in the gas-liquid mixture is approximately 15 wt % or more, the two-stage system as disclosed in EP 0212744A is employed. This system includes the medium-pressure decomposition column of from 15 to 20 bar and the low-pressure decomposition column of from 2 to 5 bar. The system including only the low-pressure decomposition column is used if the total amount of residual ammonia and carbon dioxide is less than 15 wt %.

In the purification system D, ammonia and carbon dioxide remaining in the gas-liquid mixture are removed. The heat required for that removal can be obtained from the LP steam generated in the condenser E as described below. The pressure of the LP steam is decided by the operation temperature of the condenser E. As the operation pressure in the synthesis zone is higher, the temperature of the condenser E is higher and the pressure of the LP steam to be generated is also higher. The pressure of LP steam is generally between 4 and 6 bar (between 151 and 164° C.).

In the purification system D, such LP steam is used for the heating, but the temperature that can be attained by the medium-pressure decomposition column and the low-pressure decomposition column (especially, the medium-pressure decomposition column) is limited. If the saturated temperature of the steam and the process temperature are different by 10° C., the temperature of the medium-pressure decomposition column heater can be increased up to 141° C. in the case of the LP steam of 5 bar and up to 154° C. in the case of the LP steam of 6 bar. The temperature can be increased further but in this case, the heat transfer area of the heater is increased and from the economical point of view, the further temperature increase is not adopted. If the temperature of the medium-pressure decomposition column is increased, ammonium carbamate and ammonia as the unreacted residue contained in the aqueous urea solution from the medium-pressure decomposition column are decreased and the duty on the low-pressure decomposition column on the downstream side is reduced.

The aqueous urea solution obtained in the purification system D contains a small amount of ammonia and carbon dioxide. The aqueous urea solution may be sent to a urea concentration step through an aqueous urea solution line 6a. In the urea concentration step, the aqueous urea solution may be concentrated by heating in vacuum condition. The urea resulting from the concentration may be sent to a production step, where the solid urea is manufactured as a final product.

Ammonia and carbon dioxide separated in the medium-pressure decomposition column and the low-pressure decomposition column are recovered by water as the absorbent solvent in absorbers for each pressure level. The recovered solution obtained in the low-pressure absorber has the absorbing capability under the higher pressure condition, so that this recovered solution is sent to the medium-pressure absorber for condensing gas from the medium-pressure decomposition column and used as the absorbent solvent. The obtained recovered solution, which absorbs ammonia and carbon dioxide which separated in the medium-pressure absorber pressurized upto the necessary pressure and then sent to the condenser E. The less water in the recovered solution obtained in medium-pressure absorber contributes to higher conversion ratio into urea in the synthesis step. Thus, the smaller amount of water sent to the low-pressure absorber is therefore preferable. The water to be sent to the low-pressure absorber can be reduced by reducing the unreacted substances separated in the low-pressure decomposition column. To reduce the unreacted substances in the low-pressure decomposition column, preferably, a larger amount of unreacted substances is separated in the medium-pressure decomposition column, and this can be achieved by increasing the temperature in the medium-pressure decomposition column. For synthesizing urea, it is preferable to remove as many unreacted substances as possible by increasing the temperature of the medium-pressure decomposition column. The method of heating the medium-pressure decomposition column without using the steam generated in the urea synthesis step may be adopted.

The unreacted substances (recovered solution) recovered in the purification system D are introduced into the condenser E through recovered unreacted substance lines 6b and 6c. The decomposed gas used in the shell-and-tube heat exchanger C to heat the gas-liquid mixture (a portion of the decomposed gas has been condensed and turned into the gas-liquid mixture) is introduced into the condenser E through a decomposed gas line 5b. In the condenser E, the unreacted substances and the decomposed gas are cooled by the cooling medium to be condensed, so that the condensate is obtained (condensation step). The N/C in the condensate obtained in the condenser E is preferably from 2.5 to 3.5, more preferably from 2.8 to 3.2.

Ammonia and carbon dioxide introduced into the condenser E react with each other to produce ammonium carbamate, and a portion of ammonium carbamate is turned into urea through the dehydration reaction. Thus, the resulting condensate is preferably retained in the condenser E for a certain length of time (for example 25 minutes). Since the condensate can be retained in the condenser E for a sufficient period of time, the bubble column type vertical condensation reactor (also called condenser) is preferably used. The vertical type condensation reactor is preferably the one disclosed in Patent Literature 3, for example.

The cooling medium of the condenser E is, for example, water. By supplying water from a boiler to a condenser cooling medium introduction line 31, the LP steam (from 4 to 6 bar) is discharged through a condenser cooling medium discharge line 32. As described above, the LP steam is usually used to heat the medium-pressure decomposition column and the low-pressure decomposition column.

The condensate obtained in the condenser E still contains the unreacted raw materials and therefore is introduced into the reactor A through the condensate introduction line 7a and the raw material introduction line 1a. As described above, the pressure in the reactor A is higher than the pressure in the condenser E; therefore, it is preferable to provide the ejector 12 which uses as the driving fluid at least a portion of ammonia to be introduced into the reactor as the raw material. The off gas (uncondensed gas containing mainly ammonia, carbon dioxide and inert gas) generated from the condenser E is sent to the purification system D through an off gas line 7b.

Some of the unreacted substances (recovered solution) recovered in the purification system D can be introduced into the shell-and-tube heat exchanger C together with the decomposed gas from the stripper B through a recovered unreacted substance line 6d. This facilitates the condensation of ammonia and carbon dioxide in the shell-and-tube heat exchanger C. In regard to the mixing proportion of the recovered solution, the amount of solution to be introduced into the shell-and-tube heat exchanger C is preferably not more than 30 wt %, more preferably not more than 20 wt %, of the entire recovered solution. Introducing too much recovered solution to the shell-and-tube heat exchanger C tends to generate more off gas from the condenser E. In another possible method, all the recovered solution is introduced into the condenser E and the off gas is washed in the scrubber (packed bed) above the condenser E, and the solution in which ammonia and carbon dioxide contained in the off gas are partly dissolved is sent to the shell-and-tube heat exchanger C.

According to the present invention, the unreacted substances remaining in the urea synthesis solution discharged from the stripper B can be separated efficiently and the condenser E can be reduced in size. By removing as many unreacted substances as possible in the medium-pressure decomposition column, the water required in the purification system D can be reduced and accordingly, urea can be manufactured more efficiently.

DESCRIPTION OF REFERENCE SYMBOLS

A Reactor
B Stripper
C Shell-and-tube heat exchanger
Ci Tube inlet
Co Tube outlet
D Purification system
E Condenser
1 Ammonia introduction line
1a Raw material introduction line
2 Carbon dioxide introduction line
2a Carbon dioxide introduction line
2b Carbon dioxide introduction line
3a Synthesis mixture line
4a Urea synthesis solution line
4b Decomposed gas line
4c Gas-liquid mixed phase fluid line
5a Gas-liquid mixed phase fluid line
5b Decomposed gas line
6a Aqueous urea solution line
6b Recovered unreacted substance line
6c Recovered unreacted substance line
6d Recovered unreacted substance line
7a Condensate introduction line
7b Off gas line
11 Control valve
12 Ejector
21 Stripper heating medium introduction line
22 Stripper heating medium discharge line
31 Condenser cooling medium introduction line
32 Condenser cooling medium discharge line

The invention claimed is:

1. A urea manufacturing method comprising:
a synthesis step of reacting carbon dioxide and ammonia in a reactor under a condition of excessive ammonia, thereby providing a synthesis mixture containing urea, ammonium carbamate, water, unreacted ammonia, and unreacted carbon dioxide;
a decomposition step of decomposing the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea;
a pressure reduction step of placing the urea synthesis solution under reduced pressure, thereby providing a gas-liquid mixture;
a heating step of heating the gas-liquid mixture with the decomposed gas;
a purification step of separating water and unreacted substances including ammonia and carbon dioxide from the heated gas-liquid mixture, thereby providing a purified urea and water and recovering the separated water and unreacted substances;
a condensation step of condensing the decomposed gas after heating the gas-liquid mixture in a condenser together with at least a portion of the water and unreacted substances recovered in the purification step that is introduced through a first recovered unreacted substance line directly connected to the condenser, thereby providing a condensate; and
a condensate introduction step of introducing the condensate to the reactor;
wherein in the heating step, the decomposed gas is introduced into a tube side of a shell-and-tube heat exchanger while the gas-liquid mixture is introduced into a shell side of the shell-and-tube heat exchanger; and
wherein a portion of the water and the unreacted substances recovered in the purification system is introduced into the tube side of the shell-and-tube heat exchanger through a second recovered unreacted substance line, that is directly connected to the shell-and-tube heat exchanger, together with the decomposed gas.

2. The method according to claim 1, wherein the concentration of each of ammonia and carbon dioxide contained in the gas-liquid mixture is from 10 to 15 wt %.

3. The method according to claim 1, wherein urea is synthesized in the condensation step using a bubble column vertical condensation reactor.

4. The method according to claim 1, wherein in the heating step, the decomposed gas is introduced through an upper nozzle among nozzles provided on the tube side of the shell and tube heat exchanger.

5. The method according to claim 1, wherein in the condensate introduction step, an ejector is used and the ejector uses, as a driving fluid, at least a portion of ammonia introduced into the reactor as a raw material.

6. The method according to claim 1, wherein N/C in the condensate is from 2.5 to 3.5, and N/C in the synthesis mixture is from 3.0 to 4.0.

7. The method according to claim 1, wherein not more than 30 wt % of the water and the unreacted substances recovered in the purification system is introduced into the tube side of the shell-and-tube heat exchanger.

8. A urea manufacturing apparatus comprising:
a reactor in which carbon dioxide and ammonia are reacted under a condition of excessive ammonia, thereby providing a synthesis mixture containing urea, ammonium carbamate, water, unreacted ammonia, and unreacted carbon dioxide;
a stripper that decomposes the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea;
a control valve for providing a gas-liquid mixture by placing the urea synthesis solution under reduced pressure;
a shell-and-tube heat exchanger that heats the gas-liquid mixture with the decomposed gas;
a purification system that purifies urea by separating water and unreacted substances including ammonia and carbon dioxide from the heated gas-liquid mixture, and recovers the separated water and unreacted substances;
a condenser that condenses the decomposed gas after heating the gas-liquid mixture, and at least a portion of the water and the unreacted substances recovered in the purification system that is introduced through a first recovered unreacted substance line directly connected to the condenser, thereby providing a condensate; and
a condensate introduction line that introduces the condensate to the reactor;
wherein the decomposed gas is introduced into a tube side of the shell-and-tube heat exchanger and the gas-liquid mixture is introduced into a shell of the shell-and-tube heat exchanger; and
wherein a portion of the water and the unreacted substances recovered in the purification system is introduced into the tube side of the shell-and-tube heat exchanger through a second recovered unreacted substance line directly connected to the shell-and-tube heat exchanger, together with the decomposed gas.

9. The apparatus according to claim 8, wherein the condenser is a bubble column vertical condensation reactor.

10. The apparatus according to claim 8, wherein the decomposed gas can be introduced through an upper nozzle among nozzles provided on the tube side of the shell-and-tube heat exchanger.

11. The apparatus according to claim 8, wherein the condensate introduction line is connected to an ejector, and the ejector uses as a driving fluid, at least a portion of ammonia introduced into the reactor as a raw material.

* * * * *